United States Patent [19]

Besselink et al.

[11] Patent Number: 5,507,826
[45] Date of Patent: Apr. 16, 1996

[54] PROSTHESIS WITH SHAPE MEMORY LOCKING ELEMENT

[75] Inventors: Petrus A. Besselink, Enschede, Netherlands; Rohit C. L. Sachdeva, Plano, Tex.

[73] Assignee: Memory Medical Systems, Inc., Plano, Tex.

[21] Appl. No.: 225,849

[22] Filed: Apr. 11, 1994

Related U.S. Application Data

[63] Continuation-in-part of Ser. No. 64,953, May 20, 1993, which is a continuation-in-part of Ser. No. 26,980, Mar. 5, 1993, abandoned.

[51] Int. Cl.⁶ .................................................. A61F 2/34
[52] U.S. Cl. ........................ 623/22; 623/18; 606/78
[58] Field of Search ................... 623/11, 16, 18, 623/22; 606/78, 91, 95; 602/7

[56] References Cited

U.S. PATENT DOCUMENTS

| | | |
|---|---|---|
| 3,740,839 | 6/1973 | Otte et al. . |
| 3,759,552 | 9/1973 | Levinsohn et al. . |
| 3,783,429 | 1/1974 | Otte . |
| 3,786,806 | 1/1974 | Johnson . |
| 3,861,030 | 1/1975 | Otte et al. . |
| 3,872,573 | 3/1975 | Nichols et al. . |
| 3,913,444 | 10/1975 | Otte . |
| 4,001,928 | 1/1977 | Schweiso . |
| 4,022,519 | 5/1977 | Hill . |
| 4,035,007 | 7/1977 | Harrison et al. . |
| 4,049,151 | 9/1977 | Schweiso . |
| 4,149,911 | 4/1979 | Clabburn . |
| 4,170,990 | 10/1979 | Baumgart . |
| 4,198,081 | 4/1980 | Harrison et al. . |
| 4,233,690 | 11/1980 | Akins . |
| 4,798,610 | 1/1989 | Auerill et al. ........................ 623/22 |
| 4,921,499 | 5/1990 | Hoffman et al. ...................... 623/16 |
| 4,960,427 | 10/1990 | Noiles .................................. 623/22 |
| 5,049,158 | 9/1991 | Engelhardt et al. .................. 623/22 |
| 5,080,677 | 1/1992 | Shelley ................................ 623/22 |
| 5,080,678 | 1/1992 | Spotorno et al. .................... 623/22 |
| 5,092,898 | 3/1992 | Bekki et al. ......................... 623/22 |
| 5,190,546 | 3/1993 | Jervis ................................. 606/78 |

FOREIGN PATENT DOCUMENTS

| | | | |
|---|---|---|---|
| 591594 | 4/1994 | European Pat. Off. .............. 623/22 |
| 2648990 | 5/1978 | Germany . | |

OTHER PUBLICATIONS

"An Introduction to Martensite and Shape Memory", C. M. Wayman & T. W. Duerig, pp. 3–20.
"The Mechanical Aspects of Constrained Recovery", J. L. Proft & T. W. Duerig, pp. 115–129.
"The Two-Way Shape Memory Effect", J. Perkins & D. Hodgson, pp. 195–206.
"The Use of Ni-Ti as an Implant Material in Orthopedics", Dr. J. Haasters, Prof. G. v.Salis-Solio & Dr. G. Bensmann, pp. 426–444.
"An Engineer's Perspective of Pseudoelasticity", T. W. Duerig & R. Zadno, pp. 369–393.
"Wide Hysteresis Shape Memory Alloys", T. W. Duerig, K. N. Melton & J. L. Proft, pp. 130–136.

(List continued on next page.)

*Primary Examiner*—David Isabella
*Assistant Examiner*—Laura Fossum
*Attorney, Agent, or Firm*—Daren C. Davis

[57] ABSTRACT

The present invention is a prosthesis (10) for replacing a body part which includes a first element (16) adapted to receive at least a portion of a second element (18) in an operative manner. The present prosthesis (10) also includes a variable locking ring (20) made of a shape memory material having a transformation temperature range ("TTR"). The locking ring (20) is used to allow insertion of the second element (18) into the first (16) at least at temperatures below the TTR and to lock the elements (16, 18) together at least at temperatures above the TTR. With it at a temperature below its TTR, the locking ring (20) is positioned between the two elements (16, 18). With it so positioned, the locking ring (20) is adapted to interlock the elements (16, 18) together at temperatures above its TTR by at least attempting to change its shape.

3 Claims, 3 Drawing Sheets

OTHER PUBLICATIONS

"Shape Memory Alloy Tube and Pipe Coupling", M. Kapgan & K. N. Melton, pp. 137–148.

"The Design of Electrical Interconnection Systems with Shape Memory Alloys", E. Cydzik, pp. 149–157.

"Shape Memory Alloy Fastener Rings", T. Borden, pp. 158–169.

"Rotation Vector, A New Method for Representation of Three–Dimensional Deformity in Scoliosis", T. Kojima, M.D. & T. Kurokawa, M.D., Ph.D., pp. 1296–1303, Jun. 1, 1992.

"Luque–Galveston Procedure for Correction and Stabilization of Neuromuscular Scoliosis and Pelvic Obliquity: A Review of 68 Patients", Yih–Lan Gau, J. E. Lonstein, R. B. Winter, S. Koop & F. Denis, J. Spinal Disord vol. 4, No. 4, pp. 399–410, 1991.

"Das mechanische Prinzip des Fixateur externe zur dorsalen Stabilisierung der Brust–und Lendenwirbelsäule", P. Kluger & H. J. Gerner, *Unfallchirurgie* 12, pp. 68–79, 1986.

"Posterior Stabilization with an Interlaminar Clamp in Cervical Injuries: Technical Note and Review of the Long Term Experience with the Method", Neurosurgery, vol. 14, No. 3, Mar., 1984, R. O. Holness, W. S. Huestis, W. J. Howes & R. A. Langille, pp. 318–322.

Fig. 1
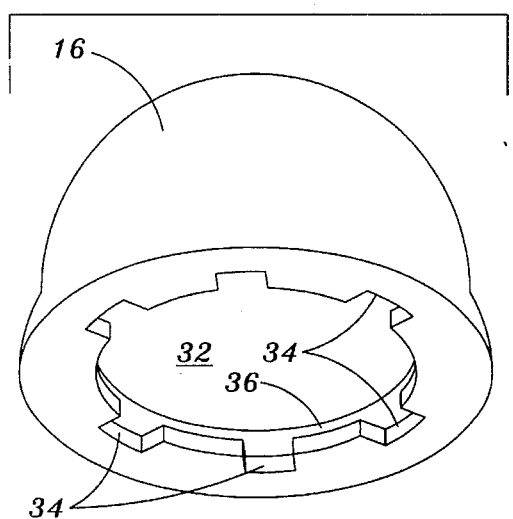
Fig. 2
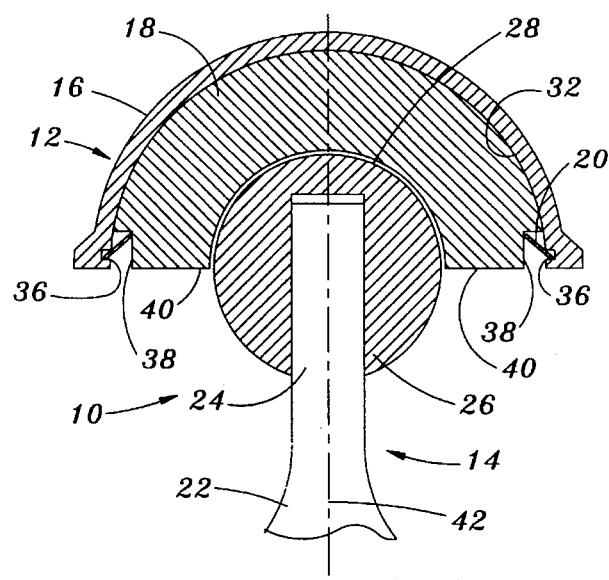
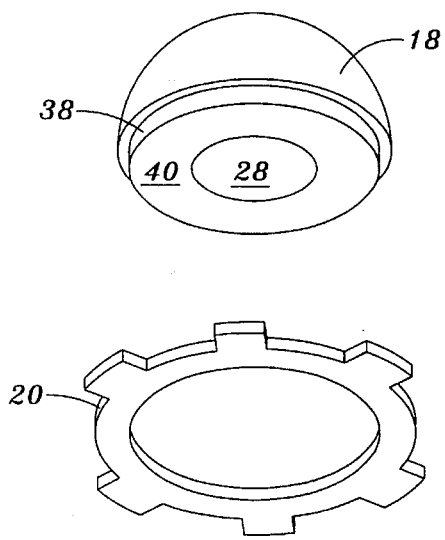
Fig. 3A
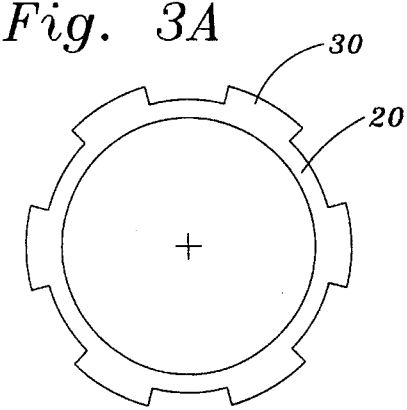
Fig. 3B
Fig. 3C

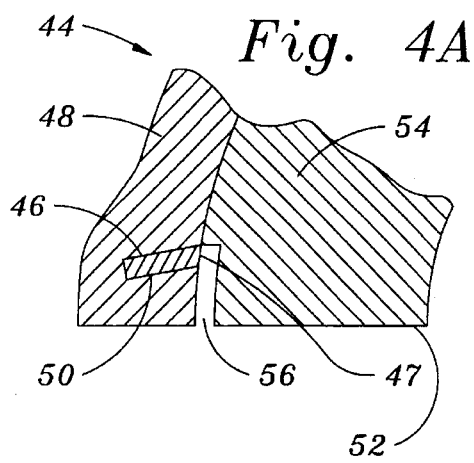
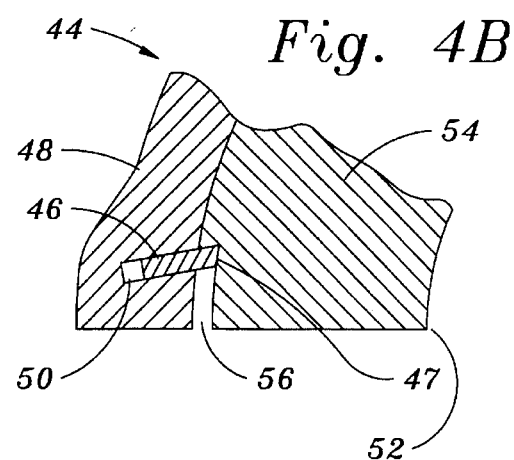
Fig. 4A    Fig. 4B
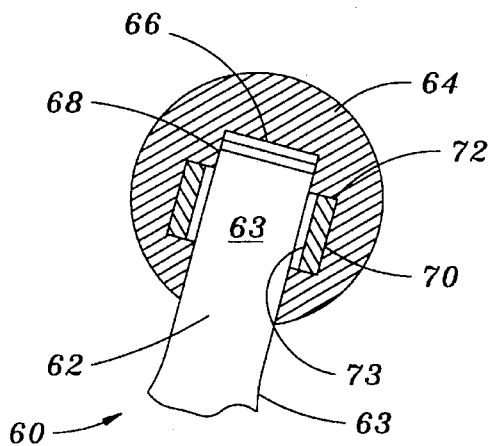
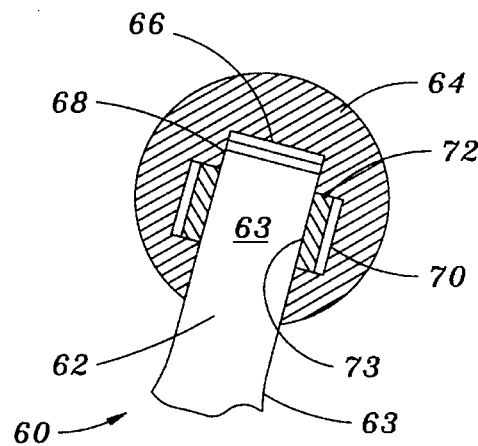
Fig. 5A    Fig. 5B
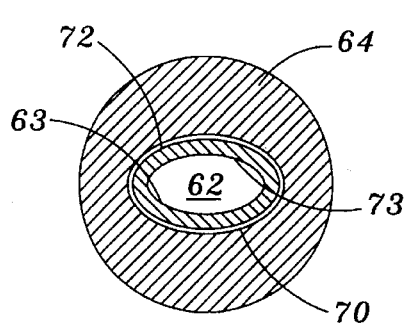
Fig. 5C
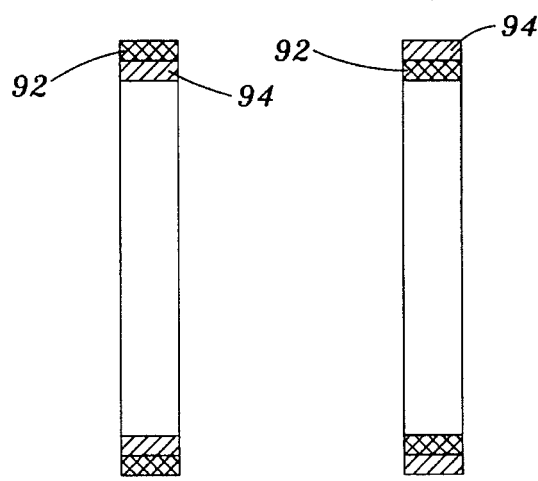
Fig. 8A    Fig. 8B

PROSTHESIS WITH SHAPE MEMORY LOCKING ELEMENT

RELATED APPLICATIONS

This application is a continuation-in-part application of U.S. patent application Ser. No. 08/064,953, filed May 20, 1993 which is a continuation-in-part application of U.S. patent application Ser. No. 08/026,980, filed Mar. 5, 1993, now abandoned.

FIELD OF THE INVENTION

The present invention is related to prostheses and components thereof, more particularly to body joint prostheses and even more particularly to the use of a shade memory element for interlocking elements of body joint prostheses.

BACKGROUND OF THE INVENTION

Prostheses have been developed to replace a wide variety of body parts. Some prostheses, in particular prosthetic body joints, include at least one element anchored to bone. When the bone anchoring element is first implanted, it is preferable that no external forces be applied to the embedded element, and therefore to the bone, until the bone has had time to heal. By giving it this time, the bone is more likely to grow and bond with the anchoring element, and thereby increase the strength of the bond between the prosthesis and the bone. In general, bone is less likely to bond to an embedded element if external forces are applied soon after implantation.

In time, one or more elements of the prosthesis will eventually wear out or otherwise need replacing. Body joint prostheses typically wear out faster than other prostheses because of the bearing loads they receive. Such bearing loads also make it more difficult for the bone, if damaged during the replacement operation, to heal and bond as strongly with the prosthesis. During surgery to replace the worn out element, it is thus better to leave the bone undisturbed. Prostheses used to replace high load bearing joints like hid joints may need to be repaired or replaced as often as every fifteen years of use or less. Recognizing that the present invention is applicable to other body parts as well, hip joint prostheses are discussed here for the purpose of example only.

Hip joint prostheses generally have an acetabular and a femoral component. The acetabular component typically includes a cup shaped metal shell which is anchored in the patients acetabulum and a polymeric socket liner seated in the metal shell. The femoral component typically include, a hip stem which is embedded in the top of the patients femur and a metal or ceramic ball mounted on the neck of the stem. The ball and socket articulate one inside the other and are directly load bearing together. It is usually the polymeric liner that wears out the fastest and needs replacement first. Such replacement operations are typically very traumatic for the patient. If the bone-to-prosthesis bond is broken or otherwise weakened during the operation, the patient may need to remain in bed or otherwise limit their mobility, such as by being confined to a wheelchair, to eliminate or at least significantly reduce applying bearing loads to the prosthesis and thereby to the bone. Having to remain so immobilized only adds to the suffering and inconvenience endured by the patient.

Body joint prostheses have been designed so as to permit replacement of load bearing components. For example, many hip joint prostheses are modular in construction with a variable locking system that allows a worn liner to be removed from the shell and a new liner reinstalled. One chronic problem with prior modular joint prostheses is that even though they may remain interlocked, micromovement between the liner and shell still occurs during use. This micromovement has been found to generate wear particles mainly from the polymeric liner. In addition to speeding up the wear process, it has been found that sufficient quantities of these wear particles can generate a bone disease called osteolysis. Osteolysis destroys healthy bone, and since it seldom causes pain, in many cases the disorder has caused sufficient bone damage to weaken healthy bone to the point of becoming susceptible to fracturing before the patient knows anything is wrong. With prior locking systems, the liner is typically snapped in and out of the shell. While some are designed to inhibit micromovement more than others, there is still a need to further limit such micromovement in order to keep the bone healthy and lengthen the life of the joint prostheses.

By making the cud component of single piece or unitary construction (i.e., permanently fixing the shell and liner together), such micromovement and the resulting wear particles can be eliminated. Some prior hid joint prostheses have cup components with the liner permanently molded in the shell. However, with such single piece cup components, if the liner wears out, the shell must be removed from the bone. Replacing the entire cud component requires more invasive surgery (e.g., resecting the bone) than simply replacing the liner. Along with the additional pain and inconvenience associated with such invasive surgery, there is a risk that the bone will reject the new prosthesis and not bond with the new cud component.

Therefore, there is a need for a prosthesis of modular construction which behaves more like one of single piece construction. More particularly, there is a need for a bone anchored prosthesis having components that can be readily replaced without substantial trauma to the bone, and at the same time, one that is less likely to permit micromovement between its components.

SUMMARY OF THE INVENTION

An objective of the present invention is to provide a prosthesis of modular construction which behaves more like one of single piece construction.

Another objective of the present invention is to provide a bone anchored prosthesis having elements that can be readily replaced without substantial trauma to the bone.

Still another objective of the present invention is to provide a body joint prosthesis having at least one bearing surface that can be replaced without substantial trauma to the bone-to-prosthesis bond.

Yet another objective of the present invention is to provide such a body joint prosthesis which is less likely to generate weal particles.

A further objective of the present invention is to provide a body joint prosthesis which is less likely to cause osteolysis.

Broadly, the prosthesis of the present invention includes a first element adapted to receive at least a portion of a second element in an operative manner. The present prosthesis also includes a variable locking ring made of a shape memory material having a transformation temperature range ("TTR"), The locking ring is used to allow insertion of the second element into the first at least at temperatures below the TTR and to lock the elements together at least at temperatures above the TTR. With it at a temperature below its TTR, the locking ring is positionable between the two elements. With its so positioned, the locking ring is adapted to interlock the elements together at temperatures above its TTR by at least attempting to change its shape.

When used to replace a body joint, such as a hip, shoulder, elbow and finger joint the present prosthesis may include a cup component where the first element is a shell which is anchored to bone and the second element is a liner for the shell. In one embodiment of such a body joint prosthesis, the liner is received in the shell without the variable locking ring positioned on either element. With the shell and liner so engaged, the locking ring can be positioned between the shell and the liner at least at temperatures below its TTR. With it positioned therebetween, the locking ring is adapted to interlock and preferable limit micromovement between the shell and the liner at least at temperatures above its TTR. Such a body joint prosthesis may also include a head component where another first element is a ball adapted to articulate in a cavity formed in the liner and another second element is a stem fixable to bone. If multiple first and second elements are used, the body joint prosthesis can include variable locking rings which may be made of the same or a different shape memory material having the same or a different TTR. In addition, each ring may have the same or a different shape training and interlock its respective elements in the same or a different manner.

In another embodiment of the present invention, before the second element is inserted in the first element, the variable locking ring is operatively positioned on only one of the elements. With the ring so positioned, the second element can be inserted in the first element when the locking ring is at a temperature at least below its TTR. With the elements so engaged, the locking ring is positioned therebetween and adapted to interlock the two elements together at least at temperatures above its TTR.

Shape memory materials are generally relatively weak and pliable at least when the material is at a temperature below its TTR and relatively strong with superelastic properties at least when the material is at a temperature above its TTR. The properties of a given shape memory material typically vary within its TTR. Generally, the strength and superelastic characteristics tend to increase toward the high temperature end of its TTR and decrease toward the low temperature end. The characteristics of shape memory materials are well documented. For example, see the following published works: a book entitled *Engineering Aspects of Shape Memory Alloys*, 1990, published by Butterworth & Heinemann and edited by T. W. Duerig, K. N. Melton, D. Stockel and C. M. Wayman (ISBM No. 0- 750-61009-3), including articles therein entitled "An Introduction to Martensite and Shape Memory" by C. M. Wayman and T. W. Duerig, pages 3–20; and "The Mechanical Aspects of Constrained Recovery", by J. L. Proft and T. W. Duerig, pages 115–129, each of which are incorporated by reference herein in their entirety. The unique properties of shape memory materials enable any structure made of such a material to have one geometric configuration (i.e., shape) at a temperature below its TTR and another geometric configuration at a temperature above its TTR. For purposes of the present invention, the working or ambient temperature of the prosthesis is typically a range of temperatures, preferably those temperatures normally found in the human body. The TTR of any of the present variable locking rings may fall below or overlap the working temperature(s) of the prosthesis.

Thus, the shape memory locking ring that interlocks the prosthesis elements can be processed or trained, according to well-known techniques, to have a shape which would permit one element to be easily inserted into or removed from the other element with little, if any, applied force when the shape memory locking ring is at least at a temperature below its TTR. Likewise, in order to lock the two elements together, the shape memory locking ring can be processed to have a shape which would not permit one element to be removable from the other element at least at temperatures above its TTR without an excessive amount of force being applied. For example, the interlocking elements of the prosthesis may be designed such that the locking ring is prevented from changing its shape. This in turn would cause strain to develop in the shape memory material and thereby produce the forces which must be overcome in order to extract one element from the other or permit movement therebetween. It is also envisioned that instead of or in combination with the generation of such strain forces, the shape memory locking ring can be trained to have a shape which mechanically interlocks with one or both of the prosthesis elements. For example, surfaces between the ring and one or both elements may form matching ridges and grooves or threads which engage or mate with each other when the ring is at the working temperature(s) of the prosthesis.

The amount of force needed to extract one element from the other or permit movement therebetween may not only be controlled by the shape memorized but also by the shape memory material selected and its mechanical properties. By selecting a shape memory material having a TTR that falls below the working temperature of the prosthesis, the strength and superelastic characteristics of the material, and therefore the strength of the locking force, can be maximized. Lower locking forces can be obtained by choosing a shape memory material having a TTR that overlaps the working temperature(s) of the prosthesis. The desired locking force may also be obtained by varying the mechanical properties of the shape memory material, such as by material selection or processing. The mechanical properties of many shape memory materials can be varied, some to a significant degree, particularly shape memory metal alloys.

One element can be interlocked with and unlocked from the element implanted in bone with little, if any, applied force simply by changing the temperature of the applicable shape memory locking ring. The embedded element can then remain undisturbed if the one element is to be replaced or otherwise removed. This is of particular significance to bone-anchored prostheses because the strength of the anchorage can be maintained. In addition, it may be possible to supply sufficiently high forces between the two elements to substantially prevent movement even micromovement therebetween. Thus, the two interlocking elements can be made modular in construction and yet still behave as if of one piece construction.

The present locking ring can be designed for positioning between the two elements in such a way that direct contact between the shape memory material and the patients body tissue is prevented. Therefore, the present prosthesis is more likely to be compatible with a greater number of patients. Some patients have been known to have undesirable reactions to certain shape memory materials, notably the nickel in nickel-titanium shape memory alloys.

The above and other objectives, features, and advantages of the present invention will become apparent upon consideration of the detailed description and the appended drawings.

BRIEF DESCRIPTION OF THE DRAWINGS

FIG. 1 is an exploded perspective view of a cup component embodiment of a hip joint prosthesis according to the present invention;

FIG. 2 is a sectional side view of a hip joint prosthesis incorporating the cup component of FIG. 1 in an assembled and locked condition taken along lines 2—2;

FIG. 3A is a plan view of the locking ring in the prosthesis of FIG. 1 in its flat condition;

FIG. 3B is a side view of the locking ring in the prosthesis of FIG. 1 in its flat condition;

FIG. 3C is a side view of the locking ring in the prosthesis of FIG. 1 in its beveled condition;

FIG. 4A is an enlarged sectional side view of an alternative embodiment to the cup component of FIG. 1 in an unlocked condition;

FIG. 4B is an enlarged sectional side view of the cup component of FIG. 4A in a locked condition;

FIG. 5A is a sectional side view of one embodiment of the head component of FIG. 1 according to the present invention in an unlocked condition;

FIG. 5B is a sectional side view of the head component of FIG. 5A in a locked condition;

FIG. 5C is a sectional end view of the head component of FIG. 5B;

FIG. 8A is a sectional side view of a one-way shape memory locking ring according to the present invention; and FIG. 8B is a sectional side view of an alternative one-way shape memory locking ring according to the present invention.

DETAILED DESCRIPTION OF THE INVENTION

Figure 6A:
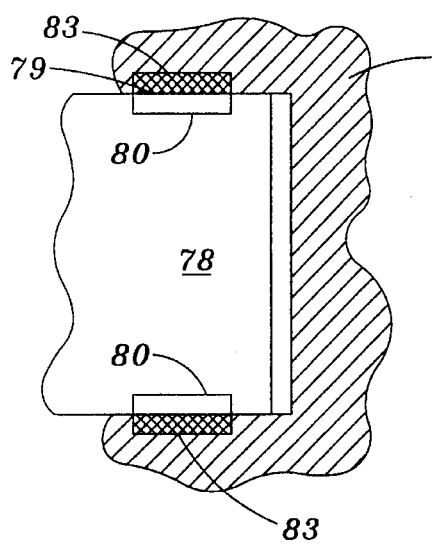
FIG. 6A is a diagrammatic sectional side view of part of two elements of a prosthesis according to the present invention in an unlocked condition.

Although the present invention is herein described in terms of specific embodiments, it will be readily apparent to those skilled in this art that various modifications, rearrangements, and substitutions can be made without departing from the spirit of the invention. The scope of the present invention is thus only limited by the claims appended hereto.

Referring to FIGS. 1 and 2, one embodiment of the present invention is a hip joint prosthesis 10 which includes an acetabular cup component 12 and a femoral head component 14. The cup component 12 has a first element or shell 16 made of a corrosion resistent metal (e.g. titanium alloys, etc . . . ) and adapted to receive a second element or socket liner 18 made of a polymeric material (e.g., ultra-high molecular weight polyethylene, UHMWPE). A first variable locking ring 20 made of a shape memory material having a first transformation temperature range ("TTR") is used to lock the liner 18 and shell 16 together and substantially prevent micromovement therebetween. The head component 14 has a hip stem 22 made of a suitable corrosion resistant metal with a neck 24 mounting a ball 26 made of a suitable metal or ceramic material. Ball 26 is adapted to articulate within a cavity 28 formed in socket liner 18.

Referring to FIGS. 3A–C, the shape memory locking ring 20 is trained to be generally flat (see FIG. 3B) at least at temperatures below its TTR and beveled (see FIG. 3C) at least at temperatures above its TTR. Ring 20 has a plurality of locking tabs 30 circumferentially spaced around its outer edge. The shell 16 has an inner surface 32 with a plurality of circumferentially spaced insertion notches 34 formed therein. A circumferential retaining slot 36 is formed in the inner surface 32 between any two adjacent notches 34 and is adapted to receive one of the tabs 30. The socket liner 18 has a circumferential groove 38 formed in its outer edge which is adapted to permit the ring 20 to be seated therearound, at least when the ring is at temperatures below its TTR.

When the liner 18 is seated in shell 16, groove 38 has a depth, as measured from its exposed surface 40, at least equal to the depth of slots 36 in shell 16. With the liner 18 so received in shell 16 and the ring 20 in its substantially flat condition (see FIG. 3B), ring 20 is adapted for being positioned down into groove 38 when each of the tabs 30 are lined up over one of the notches 34. To interlock the liner 18 and shell 16, ring 20 is positioned down into groove 38 and notches 34 and then rotated around central axis 42 until each of the tabs 30 is at least partially received in one of the slots 36. The insertion and rotation of ring 20 should be accomplished before ring 20 warms up to a temperature that causes it to substantially change shape (i.e., become beveled). Once the tabs 30 and slots 36 are so operatively disposed, the ring 20 can be allowed to warm up to a temperature above its TTR. As it warms up to such a temperature, ring 20 changes from laying generally flat and perpendicular to axis 42 to being beveled at an acute angle from axis 42, when at least partially unconstrained. Generally, the closer groove 38 and slots 36 are in depth (relative to surface 40), the less ring 20 will be able to transform to its memorized (i.e.,beveled) shape, and thus, the greater the force ring 20 will be able to apply between shell 16 and liner 18, when ring 20 does transform. The depth of groove 38 in relation to slot 36, as shown in FIG. 1, is exaggerated for illustrative purposes. Cup component 12 is preferably designed with the groove 38 and slots 36 having the same depth so that ring 20 is constrained to remain at its low temperature shape (i.e., substantially flat) even at temperatures above its TTR. Being so constrained, the forces exerted by ring 20 can be maximized to not only interlock the shell 16 and insert 18 but also to limit micromovement therebetween. Ring 20 is installed with shell 16 and insert 18 interlocked in this manner after or preferably before the shell 16 is implanted in a patient's acetabulum.

Briefly, the working temperature or temperature range (e.g., temperatures normally found in the human body) of any shape memory portion of the present invention may be within or above the TTR of the shape memory material(s) being used. The TTR for many shape memory materials, especially shape memory metal alloys, can often be adjusted to compensate for a particular ambient temperature. For some applications, it may be preferable for each shape memory portion of the present invention to have a TTR which falls below the working temperature(s). In other applications, it may be preferable for the TTR to overlap the working temperature(s).

While the present invention is not to be limited to the use of any particular shape memory material, shape memory metals, particularly binary alloys of titanium (Ti) and nickel (Ni) as well as Ni and Ti alloyed with, for example, niobium (Nb), iron (Fe), cobalt (Co), copper (Cn) or manganese (Mn), are of particular interest. With respect to most shape memory metals, two basic crystal structures exist, martensite below the TTR and austenite above the TTR. A combination of both structures, to varying degrees, may exist within the TTR. Generally, martensite is relatively weak and pliable, and austenite is relatively strong with superelastic properties. If the shape memory metal is in the martensitic stage, it will need to be heated to transform to austenite. If the shape memory metal is in the austenitic stage, it will need to be cooled to transform to martensite. When the ambient temperature is within the TTR, the actual structure of the shape memory metal is dependent on its temperature history. When the structure of the shape memory metal is not all but mostly austenite, it can still exhibit superelastic properties. When the structure of the shape memory metal is all or mostly martensite, it is comparatively weaker and more pliable than the austenite structure, but it can still exhibit some elastic properties (i.e., strained to produce an applied force). Some shape memory metals, commonly known as wide hysteresis alloys can have a wide TTR. With these materials, it is possible to use the martensitic structure during insertion at ambient temperature, thereby enabling adjustment without cooling. Once the adjustment is completed, the memory material is temperature cycled (typically by heating above the TTR) to drop the martensite-to-austenite transformation to a temperature well below ambient temperature. The locking effect would therefore be stable, at a wide range of ambient temperatures. This type of shape memory material is particularly useful when the environment is inside a patient's body and repeated adjustment is often not necessary or desirable but additional temperature stability is.

Referring to FIGS. 4A and 4B, a modified version 44 of the previously described cup component 12 includes a variable locking ring 46 which is similar to ring 20, except that ring 46 remains beveled (see FIG. 3C) at temperatures above or below its TTR. When ring 46 changes from a temperature below its TTR (see FIG. 4A) to a temperature above its TTR (see FIG. 4B), its inside diameter becomes smaller. Cup component 44 includes a shell 48 similar to shell 16 but with slots 50 which are inclined relative to surface 52 and adapted to receive the beveled ring 46. Cup component 44 also includes a socket liner 54, similar to liner 18, with a circumferential groove 56 around its outer edge. Ring 46 includes a plurality of locking tabs (not shown) like tabs 30, and shell 48 includes a plurality of matching insertion notches (not shown) similar to notches 34 so that ring 46 can be installed in shell 48 in the same manner as previously described for the installation of ring 20 in shell 16. Having been so trained, as the ring 46 transforms with the increase in temperature, the inner edge 47 extends out of shell 48 as the inside diameter of ring 46 becomes smaller, until edge 47 contacts liner 54 and further movement of ring 46 is constrained. Because it remains beveled, ring 46 pushes liner 54 back against shell 48 after ring 46 contacts it. Depending upon the force exerted by ring 46 as it attempts to transform to its preprogrammed shape, edge 47 may dig into liner 54 at the bottom of groove 56, as shown in FIG. 4B. Similar to that previously described for cup component 12, the force exerted between liner 54 and shell 48, and thus the degree of interlocking and micromovement between the two, is dependent upon a number of factors including the properties of the shape memory material chosen for ring 46, the inside diameter ring 46 would reach if unconstrained, and the distance edge 47 must travel before engaging liner 54 (e.g., the size of groove 56).

Alternatively, cup component 44 may be designed with ring 46 including no locking tabs, and shell 48 including no insertion notches. Instead, ring 46 is trained to have an outside diameter that is small enough to fit within shell 48 at temperatures above its TTR and to expand completely into one continuous circumferential slot 50 upon being cooled below its TTR. Liner 54 may then be seated in shell 48 as shown and ring 46 allowed to warm up to a temperature above its TTR and interlock the liner 54 and shell 48 as previously described.

Referring to FIGS. 5A and 5B, the principles of the present invention are equally applicable to the femoral component 14 of the hip joint prosthesis 10 or components of other prostheses (not shown) including but not limited to finger, elbow, and shoulder joint prostheses. One embodiment of a femoral component 60 according to the present invention includes a neck 62 having an outer surface 63 mounting a ball 64. Ball 64 includes a cavity 66 adapted to receive the end of neck 62. Cavity 66 has an inside surface with a circumferential groove 70 formed therein. The groove 70 is adapted to receive a variable locking ring 72 made of a shape memory material having a suitable transformation temperature range ("TTR"). At temperatures below its TTR, the ring 70 has an inside diameter at least equal to, and preferably slightly larger than, the outside diameter of neck 62 (see FIG. 5A) so that neck 62 can be freely inserted or extracted from cavity 68. When allowed to warm up unconstrained, the inside diameter of ring 72 becomes smaller than the outside diameter of neck 62. With ring 72 initially positioned within groove 70 at a temperature below its TTR and with neck 62 inserted through ring 72 and into cavity 68, ball 64 and neck 62 can be interlocked together by allowing ring 72 to warm up to a temperature above its TTR. As it warms up, the ring 72 contracts and its inside surface 73 makes contact with and grips the outside surface 63 of neck 62. In this way, ring 72 is prevented from transforming to its preprogrammed shape.

Figure 7A:
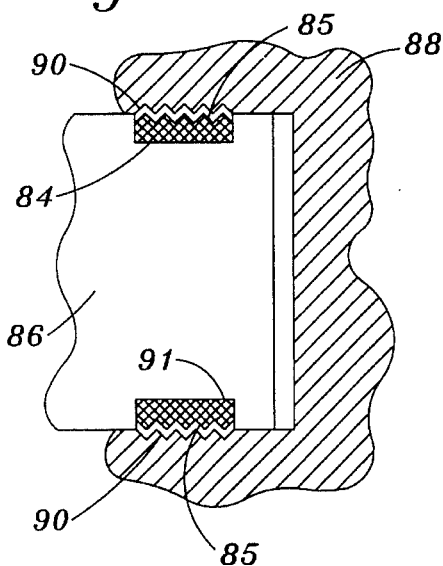
FIG. 7A is a diagrammatic sectional side view of part of two elements of an alternative prosthesis according to the present invention in an unlocked condition.
Figure 7B:
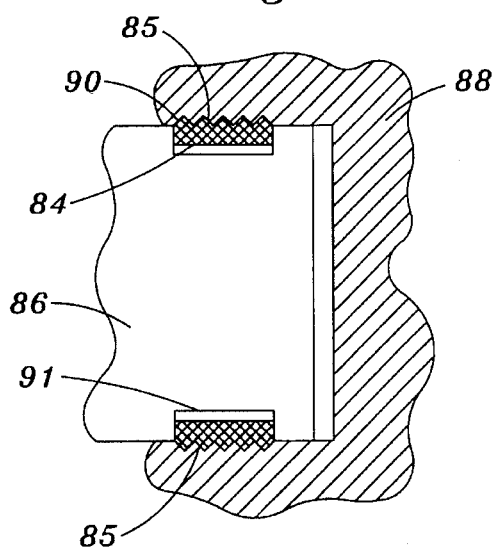
FIG. 7B is a diagrammatic sectional side view of the two prosthesis elements of FIG. 7A in a locked condition.

Referring to FIG. 5C, a mechanical locking system can be employed to aid the locking forces exerted by the ring 72 in preventing neck 62 and ball 64 from being separated. For example, the contacting surfaces 63 and 73 of neck 62 and ring 72 can be roughed (i.e., given a higher coefficient of friction), formed with mating grooves and ridges or threads (as shown in FIGS. 7A and 7B), etc . . . in order to provide an additional impediment to such separation. Relative rotation between ball 64 and neck 62 may also be inhibited in this manner as well as by making the mating portions of component 60 non-circular in cross section (i.e., Square, Oval, etc . . . ). For example, the cavity 68 and neck 62 could have matching non-circular cross sections. In addition, the groove 70 and ring 72 could likewise have matching non-circular cross sections. The preceding teachings on the use of various mechanical locking systems (i.e., roughened surfaces, mating grooves and ridges, non-circular cross sections, etc . . . ) may be applicable to aiding any variable locking ring according to the present invention in preventing two or more elements of a prosthesis from rotating or disengaging relative to one another. Variable locking rings according to the present invention, such as those herein described, may also be used to interlock operatively disposed elements of a variety of prostheses, and therefore, the present invention should not be limited to a particular type of prosthesis or elements thereof. In addition to its use as described above, locking ring 72 may also be used to interlock any number of elements, in any number of ways.

Figure 6B:
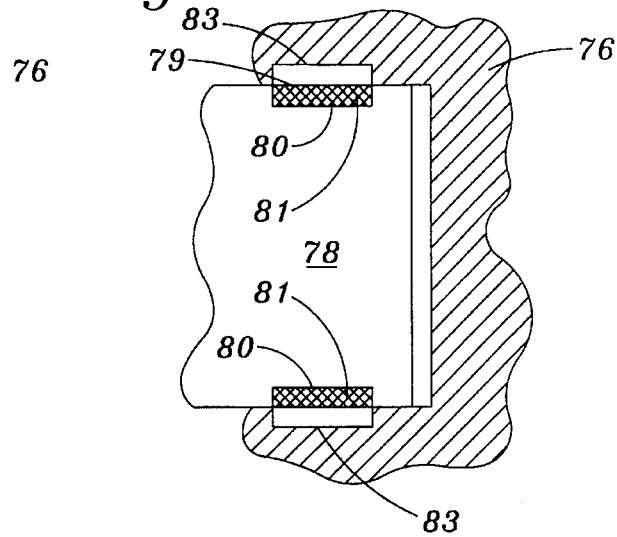
FIG. 6B is a diagrammatic sectional side view of the two prosthesis elements of FIG. 6A in a locked condition.
Figure 6C:
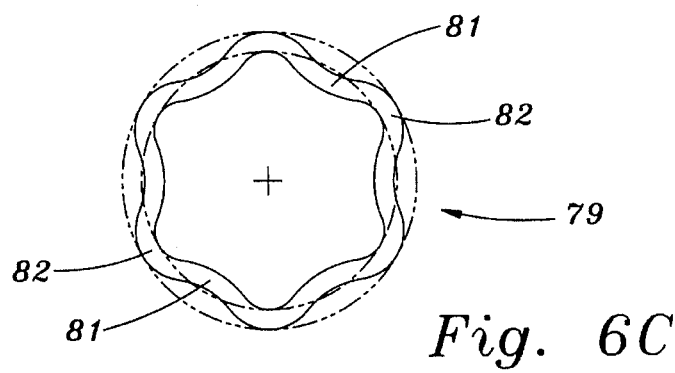
FIG. 6C is a plan view of the variable locking ring in FIG. 6B in its corrugated and locking condition.

Referring to FIGS. 6A and 6B, as an alternative to interlocking a first and second element 76 and 78 of a prosthesis by simply constricting a locking ring 79 around the second element 78, as previously described for the femoral component 60 in FIGS. 5A and 5B, a mechanical locking system may be used where the second element 78 is provided with an outer circumferential groove 80 adapted to receive only portions 81 of ring 79 (see FIG. 6B) at temperatures above its TTR while at the same time, other portions 82 of ring 79 remain in a circumferential groove 83 formed in the first element 67, similar to groove 70. In this way, the removal of element 78 from element 76 can be impeded. Referring to FIG. 6C, the ring 79 is circular in shape at temperatures below its TTR (shown in Phantom) and is trained to be corrugated in shape at temperatures above its TTR. While in its circular shape, ring 79 fits within groove 83 such that element 78 may be inserted into element 76.

Referring to FIG. 7A and 7B, an alternative variable locking ring 84 according to the present invention has a threaded outer portion 85. Ring 84 is trained to interlock a second element 86 in a first element 88 by expanding its outside diameter and bringing its threaded portion 85 into engagement with a matching threaded portion 90 of a cavity formed in the first element 88. At temperatures below its TTR, the ring 84 has a shape which keeps it within a circumferential outer groove 91 formed in the second element 86 so that the second element 86 can be inserted into and extracted from the cavity formed in the first element 88. With the second element 86 inside of the first element 88 and the ring 84 therebetween, the ring 84 is trained to expand against and its threads 85 grip the threads 90 of the first element 88 at temperatures above its TTR while a portion of ring 84 remains in groove 91.

Generally speaking, variations in geometric configuration of any shape memory element of the present invention may be accomplished in three basic ways. The shape memory element may be processed to exhibit a 2-way shaped memory, in which case simply cooling or heating pin 34 will cause it to change shape. The shape memory element may also be processed to exhibit only one-way shape memory. This would require the shape memory portion of the element to be deformed into the desired geometric configuration at a low temperature and then warmed to convert it back to its original geometric configuration. As a third method, it may be desirable for a wide hysteresis shape memory material to be used which would remain stable even at ambient temperature and would not lock in place until warmed above the ambient temperature.

Referring to FIGS. 8A and 8B, training a shape memory element to have a two-way shape memory is generally more difficult than training the material to have a one-way memory. However, a variable locking ring 92 made of a shape memory material can be modified to include a biasing ring 94 which is concentrically positioned on one or the other of the inside or the outside of ring 92. Biasing ring 94 enables the shape memory ring 92 to effectively have a two-way shape memory even if it was trained to only have a one-way memory. The biasing ring 94 may apply an expanding force or a compressive force against the shape memory ring 92 depending on whether the biasing ring 94 is positioned inside (see FIG. 8A) or outside (see FIG. 8B) the shape memory ring 92, respectively. Thus, at temperatures below the TTR of the shape memory ring 92, the biasing ring 94 is intended to apply a sufficient force to respectively expand (see FIG. 8A) or reduce (see FIG. 8B) the outside or inside diameter of shape memory ring 92 enough that one element may be inserted into another element with the rings 92, 94 therebetween. When the shape memory material warms up to a temperature above its TTR, the shape memory ring 92 is intended to exert enough force to counter any resistance exerted by the biasing ring 94 and apply enough of its own compressive force (see FIG. 8A) or expansion force (see FIG. 8B) to respectively reduce the inside diameter or expand the outside diameter of the biasing ring 94 enough that the two elements are locked together.

From the above disclosures of the general principles and detailed description of exemplary embodiments incorporating principles of the present invention, those skilled in the art will readily appreciate the various changes, modifications and alternative geometric configurations to which the present invention is susceptible. Therefore, the scope of the present invention should be limited only by the following claims and equivalents thereof.

What is claimed is:

1. A joint prosthesis comprising:

a liner having an outer circumferential edge and a groove formed therein;

a cup component having a shell, said shell having an inner surface configured to receive said liner, said liner disposed in said shell;

a first variable locking ring made of a shape memory material having a first transformation temperature range, said first variable locking ring adapted to be positioned between said shell and said liner at a temperature below said first range, said first variable locking ring having a plurality of circumferentially spaced outer locking tabs;

a plurality of circumferentially spaced insertion notches formed in said inner surface, said first ring adapted to be received in said groove when each of said tabs are aligned with one of said notches and when at a temperature below said first range;

a plurality of retaining slots formed in said inner surface between said adjacent notches;

said first ring adapted to be rotated when received in said groove at a temperature below said first range to dispose each of said tabs in said slots, said first ring adapted to apply an interlocking force at a temperature above said first range.

2. The joint prosthesis of claim 1, said first range being circular at a temperature below said second range and being corrugated at a temperature above said second range.

3. The joint prosthesis of claim 1, said first ring having a shape and a first size at a temperature below said first range and when constrained between said shell and said liner, said first ring having substantially the same shape and a second size at a temperature above said first range, said second size being different from said first size.

* * * * *